US007148176B2

(12) United States Patent
Beller et al.

(10) Patent No.: US 7,148,176 B2
(45) Date of Patent: Dec. 12, 2006

(54) PRODUCTION OF NOVEL PHOSPHANE LIGANDS AND USE IN CATALYTICAL REACTIONS

(75) Inventors: Matthias Beller, Rostock (DE); Andreas Ehrentraut, deceased, late of Rostock (DE); by Wilhelm Hubert Ehrentraut, legal representative, Vechta (DE); by Theresia Elisabeth Ehrentraut, legal representative, Vechta (DE); Christa Fuhrmann, Rostock (DE); Alexander Zapf, Rostock (DE)

(73) Assignee: Degussa AG, Dusseldorf (DE)

( * ) Notice: Subject to any disclaimer, the term of this patent is extended or adjusted under 35 U.S.C. 154(b) by 254 days.

(21) Appl. No.: 10/333,860

(22) PCT Filed: Jul. 27, 2001

(86) PCT No.: PCT/EP01/08749

§ 371 (c)(1),
(2), (4) Date: Jul. 25, 2003

(87) PCT Pub. No.: WO02/10178

PCT Pub. Date: Feb. 7, 2002

(65) Prior Publication Data

US 2004/0068131 A1    Apr. 8, 2004

(30) Foreign Application Priority Data

Jul. 27, 2000    (DE) ................. 100 37 961

(51) Int. Cl.
*B01J 31/00*    (2006.01)
(52) U.S. Cl. ................. 502/155; 502/162; 502/166; 502/170; 502/167; 502/200; 502/207; 502/213; 502/20; 564/15; 568/9
(58) Field of Classification Search .......... 502/155, 502/162, 166, 170, 167, 200, 207, 213; 562/20; 564/15; 568/9
See application file for complete search history.

(56) References Cited

OTHER PUBLICATIONS

Yamano et al., Enantioselective Hydrogenation of b-Keto Esters Catalyzed by P-Chiral Bis(dialkylphosphino)ethanes-Ru(II), Tetrahedron Letters, 40, 1999, 2577-2580.*
Hackett et al., Synthesis and Thermolysis of Dimethylbis(trialkylphosphine)platinum(II) Complexes in which the Phosphine Ligands Contain Adamantyl, Adamtylmethyl, and Methyl Groups, Oganometallics, 1987, 6, 403-410.*
Imamotoet al., P-Chiral Bis(trialkylphosphine) Ligands and Their Use in Highly Enantioselective Hydrogenation Reaction, J. Am. Chem. Soc. 1998, 120, 1635-1636.*
Stauffer et al., Palladium-Catalyzed Arylation of Ethyl Cyanoacetate. Fluorescence Resonance Energy Transfer as a Tool for Reaction Discovery , J. Am. Chem. Soc.; (Communication); 2001; 123(19); 4641-4642.*

Stauffer et al., Screening of Homogeneous Catalysts by Fluorescence Resonance Energy Transfer. Identification of Catalysts for Room-Temperature Heck Reactions, J. Am. Chem. Soc.; (Communication); 2001; 123(11); 2677-2678.*
Lavrova, et al., "D1(1-Adamantyl)Phosphines," *Russian J. Gen. Chem.* 65(9) Part 2:1393-1394 (1994).
Ehrentraut, et al., "A New Efficient Palladium Catalyst for Heck Reactions of Deactivated Aryl Chlorides," *Synlett* 1(11):1589-1592 (2000).
Goerlich, et al., "D1-1-Adamantylphosphin, ein Sterisch Hoich Gehindertes Sekundares Phosphin Darstellung und Reaktionen," *Phosphorus, Sulfur and Silicon* 81:141-148 (1993).
Goerlich, et al., "Di-1-Adamantylphosphine, A Highly Sterically Hindered Secondary Phosphine. Synthesis and Reactions," *Phosphorus, Sulfur and Silicon* 81:141-148 (1993)(English translation of Reference C2 above).
Hackett, et al., "Synthesis and Thermolysis of Dimethylbis(triakylphosphine)platinum(II) Complexes in Which the Phosphine Ligands Contain Adamantyl, Adamatylmethyl, and Methyl Groups," *Chemical Abstracts* 106:67470d, p. 630 (1987).
Hackett, et al., "Synthesis and Thermolysis of Dimethylbis(triakylphosphine)platinum(II) Complexes in Which the Phosphine Ligands Contain Adamantyl, Adamantylmethyl, and Methyl Groups," *Organometallics* 6:403-410 (1987).
Hermann, et al., "Palladacycles as Structurally Defined Catalysts for the Heck Olefination of Chloro- and Bromoarenes," *Angew. Chem. Int. Ed. Engl.* 34(17):1844-1848 (1995).
Imamoto, et al., "P-Chiral Bis(trialkylphosphine) Ligands and Their Use in Highly Enantioselective Hydrogenation Reactions," *J. Am. Chem. Soc.* 120:1635-1636 (1998).
Littke, et al., "A Convenient and General Method for Pd-Catalyzed Suzuki Cross-Couplings of Aryl Chlorides and Arylboronic Acids," *Angew. Chem. Int. Ed.* 37(24):3387-3388 (1998).
Ohashi, et al., "A New Synthetic Route to Unsymmetic P-Chriogenic Bisphosphine Ligands," *Tetrahedron Letters* 42: 1099-1101 (2001).
Ohashi, et al., "Highly Enantioselective Hydrogenation of α-Dehydroamino Acids by Rhodium Complexes with New Unsymmetric P-Chirogenic Bisphosphine Ligands," *Organic Letters* 3:373-375 (2001).
Patsanovsky, et al., *ZH. Obshch. Khim.* 64(8):1331-1332 (1994) (in Russian).
Patsanovsky, et al., "Adamantyl Phosphines: Bulky Substituent Effect on the Polarity Properties of Sterically Hampered Phosphines," *ZH. Obshch. Khim.* 64(8):1331-1332 (1994)(English translation of Reference C11 above).

(Continued)

*Primary Examiner*—Thurman K. Page
*Assistant Examiner*—Chukwuma Nwaonicha
(74) *Attorney, Agent, or Firm*—Michael A. Sanzo; Fitch, Even, Tabin & Flannery

(57) ABSTRACT

The present invention is directed to phosphine ligands and the use of such ligands in catalytic complexes with transition metals. The catalysts may be used in a variety of reactions and are especially useful for refining halogenoaromatics.

20 Claims, No Drawings

OTHER PUBLICATIONS

Stambuli, et al., Screening of Homogeneous Catalysts by Fluorescence Resonance Energy Transfer. Identification of Catalysts for Room-Temperature Heck Reactions, *J. Am. Chem. Soc. 123*:2677-2678 (2001).

Stauffer, et al., "Palladium-Catalyzed Arylation of Ethyl Cyanoacetate. Fluorescence Resonance Energy Transfer as a Tool for Reaction Discovery," *J. Am. Chem. Soc. 123*:4641-4642 (2001).

Wolfe, et al., "A Highly Active Catalyst for the Room-Temperature Amination and Suzuki Coupling of Aryl Chlorides," *Angew. Chem. Int. Ed. 38*(16):2413-2416 (1999).

Yamano, et al., "Enantioselective Hydrogenation of β-Keto Esters Catalyzed by P-Chiral Bis(dialkylphosphino) ethanes-Ru(II)," *Tetrahedron Letters 40*:2577-2580 (1999).

Yurchenko, et al., *Zh. Obshch. Khim.* 56(2):482-483 (1986)(in Russian).

Yurchenko, et al., "A Few Transformations of Adamantyl-1-Phosphine," *Zh. Obshch. Khim.* 56(2):482-483 (1986)(English translation of Reference C17 above).

Zapf, et al., "A New Highly Efficient Catalyst System for the Coupling of Nonactivated and Deactivated Aryl Chlorides with Arylboronic Acids," *Angew. Chem. Int. Ed. 39*:4153-4155 (2000).

* cited by examiner

PRODUCTION OF NOVEL PHOSPHANE LIGANDS AND USE IN CATALYTICAL REACTIONS

CROSS REFERENCE TO RELATED APPLICATIONS

The present application represents U.S. national stage of international application PCT/EP01/08749, with an international filing date of Jul. 27, 2001, and which was published in German under PCT Article 21(2) on Feb. 7, 2002. The international application claims priority to German application 100 37 961.3, filed on Jul. 27, 2000.

The present invention relates to novel phosphine ligands, to their preparation and to their use in catalytic reactions, especially for refining halogenoaromatics.

Halogenoaromatics, including especially chloroaromatics, are intermediates which have a variety of applications in the chemical industry and are used as precursors for the preparation of agricultural intermediates, pharmaceuticals, dyestuffs, materials, etc. Vinyl halides are also important intermediates which are used as precursors for polymer monomers and the above-mentioned products.

Catalysts frequently used for the functionalization of halogenoaromatics or vinyl halides to give aromatic olefins or dienes (Heck reaction, Stille reaction), biaryls (Suzuki reaction), alkynes (Sonogashira reaction), carboxylic acid derivatives (Heck carbonylation) and amines (Buchwald-Hartwig reaction) are those of palladium and nickel. Palladium catalysts are generally advantageous in terms of the breadth of applicability of coupling substrates and in some cases the catalyst activity, while nickel catalysts have advantages in the area of the conversion of chloroaromatics and vinyl chlorides and the price of the metal.

Palladium and nickel catalysts used to activate and otherwise refine halogenoaromatics are palladium(II) and/or nickel(II) as well as palladium(0) and/or nickel(0) complexes, although it is known that palladium(0)/nickel(0) compounds are the actual reaction catalysts. In particular, according to literature sources, coordinatively unsaturated 14-electron and 16-electron palladium(0)/nickel(0) complexes stabilized with donor ligands such as phosphines are formulated as active species.

It is also possible to dispense with phosphine ligands when using iodides as educts in coupling reactions. However, aryl and vinyl iodides are very expensive starting compounds and moreover produce stoichiometric amounts of iodine salt waste. More cost-effective educts for the Heck reaction, such as aryl bromides or aryl chlorides, require the use of stabilizing and activating ligands in order to become effective in catalytic production.

The catalyst systems described for olefinations, alkynylations, carbonylations, arylations, aminations and similar reactions often have satisfactory catalytic turnover numbers (TONs) only with uneconomic starting materials such as iodoaromatics and activated bromoaromatics. Otherwise, in the case of deactivated bromoaromatics and especially in the case of chloroaromatics, it is generally necessary to add large amounts of catalyst—usually more than 1 mol %—to achieve industrially useful yields (>90%). In addition, because of the complexity of the reaction mixtures, simple catalyst recycling is not possible, so the recycling of the catalyst also incurs high costs, which are normally an obstacle to realization on the industrial scale. Furthermore, particularly in the preparation of active substances or active substance precursors, it is undesirable to work with large amounts of catalyst because of the catalyst residues left behind in the product. More recent active catalyst systems are based on cyclopalladized phosphines (W. A. Herrmann, C. Brossmer, K. Öfele, C.-P. Reisinger, T. Priermeier, M. Beller, H. Fischer, Angew. Chem. 1995, 107, 1989; Angew. Chem. Int. Ed. Engl. 1995, 34, 1844) or mixtures of sterically exacting arylphosphines (J. P. Wolfe, S. L. Buchwald, Angew. Chem. 1999, 111, 2570; Angew. Chem. Int. Ed. Engl. 1999, 38, 2413) or tri-tert-butylphosphine (A. F. Littke, G. C. Fu, Angew. Chem. 1998, 110, 3586; Angew. Chem. Int. Ed. Engl. 1998, 37, 3387) with palladium salts or palladium complexes.

However, even with these catalysts, cost-effective chloroaromatics cannot generally be activated satisfactorily from the industrial point of view, i.e. catalyst productivities (TONs) are <10,000 and catalyst activities (TOFs) are <1000 h$^{-1}$. Therefore, to achieve high yields, it is necessary to use comparatively large and hence very expensive amounts of catalyst. Thus, for example, the catalyst costs for the preparation of one kilogram of an organic intermediate with a molecular weight of 200, using 1 mol % of palladium catalyst, are more than 100 US$ at current noble metal prices, so there is clearly a need for improving catalyst productivity. Therefore, despite all the catalyst developments in recent years, only a few industrial reactions have so far been disclosed for the arylation, carbonylation, olefination etc. of chloroaromatics.

For the reasons mentioned, the object of the present invention was to satisfy the great need for novel, more productive catalyst systems which have simple ligands and do not exhibit the disadvantages of the known catalytic processes, which are suitable for the large industrial scale and which convert cost-effective chloroaromatics and bromoaromatics and corresponding vinyl compounds to the respective coupling products in high yield, with high catalyst productivity and with high purity.

This object is achieved according to the invention by the development of novel phosphine ligands of formulae Ia and Ib:

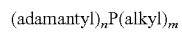

(adamantyl)$_n$P(alkyl)$_m$      Ia

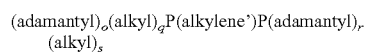

(adamantyl)$_o$(alkyl)$_q$P(alkylene')P(adamantyl)$_r$(alkyl)$_s$      Ib in which adamantyl is an adamantyl radical (IIa, IIb) bonded to the phosphorus, atom. in the 1- or 2-position:

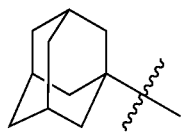

IIa

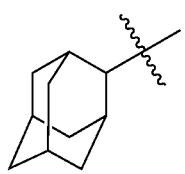

IIb alkyl is a C$_1$ to C$_{18}$ alkyl group, and alkylene' is a bridging methylene, 1,2-ethylene, 1,3-propylene, 1,4-butylene, 1,5-pentylene or 1,6-hexylene bridge, 1,2-diphenylene, 2,2'-substituted 1,1'-binaphthyl or a ferrocenyl derivative, where the alkyl group, the alkylene' group and the adamantyl radical independently of one another can have, in addition to hydrogen atoms, up to 10 substituents which independently of one another are $C_1$ to $C_8$ alkyl, O-alkyl ($C_1$–$C_8$), OH, OCO-alkyl($C_1$–$C_8$), O-phenyl, phenyl, aryl, fluorine, $NO_2$, Si-alkyl($C_1$–$C_8$)$_3$, CN, COOH, CHO, $SO_3H$, $NH_2$, NH-alkyl($C_1$–$C_8$), N-alkyl($C_1$–$C_8$)$_2$, P(alkyl($C_1$–$C_8$))$_2$, P(aryl)$_2$, $SO_2$-alkyl($C_1$–$C_6$), SO-alkyl($C_1$–$C_6$), $CF_3$, NHCO-alkyl($C_1$–$C_4$), COO-alkyl($C_1$–$C_8$), $CONH_2$, CO-alkyl($C_1$–$C_8$), NHCHO, NHCOO-alkyl($C_1$–$C_4$), CO-phenyl, COO-phenyl, CH=CH—$CO_2$-alkyl ($C_1$–$C_8$), CH=CHCOOH, PO(phenyl)$_2$, PO(alkyl($C_1$–$C_4$))$_2$, $PO_3H_2$, PO(O-alkyl ($C_1$–$C_6$))$_2$ or $SO_3$(alkyl($C_1$–$C_4$)), aryl being an aromatic with 5 to 14 ring carbon atoms and it being possible for one or more ring carbon atoms to be replaced by nitrogen, oxygen and/or sulfur atoms to give a 1- to 13-membered heteroaromatic containing ring carbon atoms, where n is a number between 1 and 3 and m is a number between 0 and 2, it being necessary to satisfy the condition n+m=3, and where o and r are the number 1 or 2 and q and s are the number 0 or 1, it being necessary to satisfy the conditions o+q=2 and r+s=2.

The phosphine ligands used according to the invention are especially compounds of formulae Ia and Ib in which adamantyl is an adamantyl radical (IIa, IIb) bonded to the phosphorus atom in the 1- or 2-position and alkyl is a $C_1$ to $C_{12}$ alkyl group. Alkylene' is preferably a bridging 1,2-ethylene, 1,3-propylene or 1,4-butylene bridge, 1,2-diphenylene, 2,2'-substituted 1,1'-binaphthyl or a ferrocenyl derivative.

Preferably, the alkyl group, the alkylene' group and the adamantyl radical independently of one another can have, in addition to hydrogen atoms, up to 5 substituents which independently of one another are $C_1$ to $C_8$ alkyl, O-alkyl ($C_1$–$C_8$), OH, OCO-alkyl($C_1$–$C_8$), O-phenyl, phenyl, aryl, fluorine, Si-alkyl($C_1$–$C_8$)$_3$, COOH, $SO_3H$, $NH_2$, NH-alkyl ($C_1$–$C_8$), N-alkyl$_2$($C_1$–$C_8$), P(alkyl($C_1$–$C_8$))$_2$, P(phenyl)$_2$, $CF_3$, NHCO-alkyl($C_1$–$C_4$), COO-alkyl($C_1$–$C_8$), $CONH_2$, CO-alkyl($C_1$–$C_8$), COO-phenyl, PO(phenyl)$_2$, PO(alkyl ($C_1$–$C_4$))$_2$, $PO_3H_2$ or PO(O-alkyl ($C_1$–$C_6$))$_2$, aryl being an aromatic with 5 to 14 ring carbon atoms and it also being possible for one or more ring carbon atoms to be replaced by heteroatoms from the group comprising nitrogen, oxygen and sulfur atoms to give a heteroaromatic with 4 to 13 ring carbon atoms.

Heteroaromatic radicals can be e.g. at least five-membered rings containing 1 to 13 ring carbon atoms and up to 4 nitrogen atoms and/or up to 2 oxygen or sulfur atoms. Preferred heteroaromatic-aryl radicals contain one or two nitrogen heteroatoms or one oxygen heteroatom or one sulfur heteroatom or one nitrogen heteroatom and one oxygen heteroatom or sulfur heteroatom.

Particularly preferred phosphine ligands according to the invention are compounds of formulae Ia and Ib in which adamantyl is an adamantyl radical (IIa, IIb) bonded to the phosphorus atom in the 1- or 2-position, alkyl is a $C_1$ to $C_{12}$ alkyl group and alkylene' in formula Ib is a bridging 1,2-ethylene, 1,3-propylene or 1,4-butylene bridge, where the alkyl group, the alkylene' group and the adamantyl radical independently of one another can have, in addition to hydrogen atoms, up to 3 substituents which independently of one another can be $C_1$ to $C_8$ alkyl, O-alkyl($C_1$–$C_8$), OH, OCO-alkyl($C_1$–$C_8$), O-phenyl, phenyl, COOH, $SO_3H$, $NH_2$, P(alkyl($C_1$–$C_8$))$_2$, P(phenyl)$_2$, COO-alkyl($C_1$–$C_8$), $CONH_2$ or PO(phenyl)$_2$.

The invention also provides the preparation of the novel phosphine ligands. They are synthesized analogously to known preparative routes for alkylphosphines. Such synthetic pathways are described for example in Houben-Weyl, Methoden der organischen Chemie, 1963, volume XII, 1, p. 33. In general, the novel phosphine ligands described here are prepared by reacting a dihalogenoadamantyl-phosphine or halogenodiadamantylphosphine with metal-organic reagents (for example alkyllithium, alkylmagnesium, alkylzinc or alkylcopper reagents). Particularly suitable halogenoadamantylphosphines are the corresponding chlorine compounds. Another synthetic route for the preparation of the ligands according to the invention is to react alkali metal adamantylphosphides or alkali metal diadamantylphosphides with organic electrophiles such as alkyl halides or pseudohalides, aldehydes or epoxides.

In general, diadamantylalkylphosphines can be synthesized according to the following instructions: A solution of 18 mmol of R—M in THF or hexane is added dropwise to a solution of 15 mmol of diadamantylchloro-phosphine in 250 ml of absolute THF, M being lithium or MgHal and Hal being chlorine, bromine or iodine. The mixture is refluxed for two hours. It is worked up at room temperature with degassed aqueous ammonium chloride solution and diethyl ether. The solvents are distilled off and the residue is distilled under high vacuum or chromatographed on silica gel 60 with hexane/ethyl acetate mixtures.

These instructions can be used to prepare e.g. the following preferred ligands:
di(1-adamantyl)methylphosphine,
di(1-adamantyl)-i-propylphosphine,
di(1-adamantyl)-n-butylphosphine,
di(1-adamantyl)-t-butylphosphine,
di(1-adamantyl)-n-hexylphosphine,
di(1-adamantyl)cyclohexylphosphine,
di(1-adamantyl)benzylphosphine,
di(1-adamantyl)pentafluoroethylphosphine,
di(3-aminoadamant-1-yl)-n-butylphosphine,
di(3-acetyladamant-1-yl)-n-butylphosphine,
di[3-(p-hydroxyphenyl)adamant-1-yl]methylphosphine,
di(2-adamantyl)-i-propylphosphine,
di(2-adamantyl)-n-butylphosphine,
di(2-adamantyl)-t-butylphosphine,
di(2-adamantyl)cyclohexylphosphine.

In general, adamantyldialkylphosphines can be synthesized according to the following instructions:

A solution of 15 mmol of a dialkylchlorophosphine in THF is added dropwise to a solution of 35 mmol of adamantyl-M in 400 ml of absolute THF or hexane, M being lithium or MgHal and Hal being chlorine or bromine. The mixture. is refluxed for four hours. It is worked up at room temperature with degassed aqueous ammonium chloride solution and diethyl ether. The solvents are distilled off and the residue is distilled under high vacuum or chromatographed on, silica gel 60 with hexane/ethyl acetate mixtures.

These instructions can be used to prepare e.g. the following preferred ligands:
(1-adamantyl)di-t-butylphosphine,
(1-adamantyl)dicyclohexylphosphine,
(2-adamantyl)di-n-butylphosphine.

In general, bis(diadamantylphosphino)alkanes can be synthesized according to the following instructions:

A solution of 15 mmol of M-alkylene-M in THF or hexane is added dropwise to a solution of 33 mmol of diadamantyl-chlorophosphine in 400 ml of absolute THF, M being lithium or MgHal and Hal being chlorine, bromine or iodine. The mixture is refluxed for four hours. It is worked up at room temperature with degassed aqueous ammonium chloride solution and diethyl ether. The solvents are distilled off and the residue is distilled under high vacuum-or chromatographed on silica gel 60 with hexane/ethyl acetate mixtures.

These instructions can be used to prepare e.g. the following preferred ligands:
1,2-bis[di(l-adamantyl)phosphino]ethane,
1,4-bis[di(l-adamantyl)phosphino]butane,
2,3-bis[di(l-adamantyl)phosphino]butane,
4,5-bis[di(l-adamantyl)phosphinomethyl]-2,2-dimethyl-1,3-dioxolane,
1,2-bis[di(l-adamantyl)phosphino]benzene.

According to the invention, the novel phosphine ligands are used as catalysts in combination with transition metal complexes or transition metal salts of subgroup VIII of the Periodic Table of the Elements, for example palladium, nickel, platinum, rhodium, iridium, ruthenium or cobalt. As a rule, the ligands according to the invention can be added in situ to appropriate transition metal precursor compounds and used in this form for catalytic applications.

The transition metal compounds used are preferably palladium or nickel compounds and particularly preferably palladium compounds.

It may be advantageous on occasion to prepare defined mono-, di-, tri- or tetraphosphine complexes of said transition metals first and then use these for catalytic. reactions.

It is preferable to use palladium and nickel catalysts containing the phosphines according to the invention.

It is particularly preferable to use palladium catalysts containing the ligands according to the invention. The ligands according to the invention are normally added in situ to palladium(II) salts or to palladium(II) or palladium(0) complexes. However, it may be advantageous to prepare palladium(0)- or palladium(II)-phosphine complexes of the phosphines according to the invention direct and then use these for catalytic applications. This increases the initial catalyst activity in some instances.

Examples of palladium components that can be used with the ligands according to the invention are palladium(II) acetate, palladium(II) chloride, palladium(II) bromide, lithium tetrachloropalladate (II), palladium (II) acetylacetonate, palladium(0)-dibenzylidenacetone complexes, palladium(0) tetrakis(triphenylphosphine), palladium(0) bis(tri-o-tolylphosphine), palladium(II) propionate, palladium(II) bis(triphenylphosphine) dichloride, palladium(0)-diallyl ether complexes, palladium(II) nitrate, palladium(II) chloride. bis(acetonitrile), palladium(II) chloride bis(benzonitrile) and other palladium(0) and palladium(II) complexes.

Generally, for catalytic applications, the phosphine ligand is used in excess relative to the transition metal. The ratio of transition metal to ligand is preferably from 1:1 to 1:1000. Ratios of transition metal to ligand of 1:1 to 1:100 are particularly preferred. The exact transition metal/ligand ratio to be used depends on the specific application and also on the amount of catalyst used. Thus, in general, it is conventional to use low transition metal/ligand ratios in the case of very low transition metal concentrations (<0.01 mol %) than in the case of transition metal concentrations of between 0.5 and 0.01 mol % of transition metal.

The novel phosphine ligands are thermally very stable. It. is thus possible to use the catalysts according to the invention at reaction temperatures of up to 250° C. or more. The catalysts are preferably used at temperatures of 20 to 200° C.; it has proved advantageous in many cases to work at temperatures of 30 to 180° C., preferably of 40 to 160° C. The ligands can also be used in pressure reactions without loss of activity, the operating pressure conventionally being up to only 100 bar, but preferably in the normal pressure range of up to 60. bar.

The phosphine ligands prepared according to the invention have proved particularly advantageous as ligand components for the catalytic preparation of arylated olefins (Heck reactions), biaryls (Suzuki reactions), α-aryl ketones and amines from aryl halides or vinyl halides. However, it is obvious to those skilled in the art. that other transition metal-catalyzed reactions, such as the metathesis or hydrogenation of double bonds or carbonyl compounds, especially however palladium-catalyzed and nickel-catalyzed carbonylations of aryl halides, alkynylations with alkynes (Sonogashira couplings) and cross couplings with metal-organic reagents (zinc reagents, tin reagents, etc.), can also be catalyzed with the novel catalyst systems.

For some catalytic applications, for example carbonylations, it may be advantageous to use chelating phosphine ligands, particularly important chelating phosphine ligands being those with an aliphatic $C_2$ to $C_6$ carbon bridge or with an aromatic bridge (1,2-phenylene, ferrocenyl, binaphthyl).

One particular advantage of the ligands according to the invention is the high activity which the ligands induce in the activation of cost-effective but inert chloroaromatics. As shown in the experimental Examples, palladium catalysts with the novel adamantylphosphines are significantly superior to the best existing catalyst systems of Buchwald (J. P. Wolfe, S. L. Buchwald, *Angew. Chem.* 1999, 111, 2570; *Angew. Chem. Int. Ed. Engl.* 1999, 38, 2413) and Fu (A. F. Littke, G. C. Fu, *Angew. Chem.* 1998, 110, 3586; *Angew. Chem. Int. Ed. Engl.* 1998, 37, 3387). Thus, with the catalyst systems according to the invention, it is even possible to achieve turnover numbers in the order of >10,000 with chloroaromatics as substrates and TONs of >500,000 with bromoaromatics as starting materials, making the described catalyst and ligand systems useful for large-scale industrial purposes.

The properties of the adamantylphosphines are particularly surprising. Although adamantyl radicals have been known for a long time in organic chemistry, no importance has been attached to phosphine ligands containing adamantyl groups. Consequently, alkyladamantylphosphines have not hitherto been described for catalytic applications. It was surprising to find that, in certain catalytic applications, adamantyl ligands are significantly superior to all other known phosphine ligands. For example, whereas the product yields obtained in the coupling of 4-chlorotoluene with an arylboronic acid using small amounts of catalyst (0.005 mol %) are 16 to 46% with the best palladium catalysts known hitherto, yields of >90% were obtained with the ligands according to the invention.

The phosphines prepared according to the invention can be used for the preparation of arylolefins, dienes, diaryls, benzoic acid derivatives, acrylic acid derivatives, arylalkanes, alkynes and amines. The compounds prepared in this way can be used inter alia as UV absorbers, intermediates for pharmaceuticals and agrochemicals, ligand precursors for metallocene catalysts, perfumes, active substances, and structural units for polymers.

EXAMPLES

The Examples which follow serve to illustrate the invention without implying a limitation.

General: The adamantylphosphine ligands are prepared under a protective gas (argon).

General Instructions for Synthesis of The Phosphines:

A mixture of 100 g (0.73 mol) of adamantane, 105 g (0.79 mol) of aluminium(III) chloride and 300 ml of phosphorus (III) chloride was refluxed for 5 h. The excess phosphorus (III) chloride was distilled off to leave a reddish-brown viscous substance. This was suspended in 1 l of chloroform and then hydrolyzed with 1 l of ice-water. The organic phase was dried over sodium sulfate and concentrated to dryness under vacuum (0.1 mbar). Yield: 130 g (0.37 mol, 93%) of di(1-adamantyl)phosphinyl chloride (melting point: 195° C.).

40 g of diadamantylphosphinyl chloride (0.11 mol) were placed in 600 ml of absolute tetrahydrofuran, the mixture was cooled to −14° C. with an ice-water/sodium chloride cooling mixture, and 10 g (0.26 mol) of lithium aluminium hydride were added in successive portions over 60 min. The mixture was then stirred at room temperature for 16 h and hydrolyzed at −14° C. with 200 ml of 1 N HCl solution. The organic phase was dried over sodium sulfate and concentrated to dryness under vacuum (0.1 mbar). Yield: 30 g (0.10 mol, 94%) of di(1-adamantyl)phosphine.

$^{31}$P NMR (162.0 MHz, CDCl$_3$): δ=18.2

60 g of a 20% solution of phosgene in absolute toluene were added dropwise at −14° C. to a solution of 23 g (76 mmol) of di(1-adamantyl)phosphine and 14.5 g (9.5 mmol) of 1,8-diazabicyclo [5.4.0]undec-7-ene (DBU) in 600 ml of toluene and the mixture was heated to room temperature and then stirred for 16 h. It was filtered and the solvent was distilled off under vacuum. Yield: 23 g (68 mmol, 90%) of diadamantylchlorophosphine.

$^{31}$P NMR (162.0 MHz, CDCl$_3$): δ=138.4

Example 1

Di(1-adamantyl)-n-butylphosphine (n-BuPAd$_2$)
(Variant 1)

11 ml of a 1.6 M solution of n-butyllithium in hexane (18 mmol) were added dropwise to 5.0 g (15 mmol) of diadamantylchlorophosphine in 250 ml of absolute tetrahydrofuran. The solution was refluxed for 1 h. After removal of the solvent under vacuum, the residue was distilled under vacuum.

2.6 g (7.3 mmol, 49%) of diadamantyl-n-butylphosphine were obtained.

Di(1-adamantyl)-n-butylphosphine (n-BuP(1-Ad)$_2$)
(Variant 2)

4.6 g (15 mmol) of di(1-adamantyl)phosphine were placed in 50 ml of di-n-butyl ether, and 20 ml of a 2.5 M solution of n-BuLi in toluene (50 mmol) were added. The mixture was refluxed for 1 h and cooled and 4.1 g (30 mmol) of 1-butyl bromide were added dropwise. The mixture was refluxed for 30 min, cooled and washed with saturated ammonium chloride solution (3×), the organic phase was separated off and dried over sodium sulfate and the solvent was distilled off under reduced pressure.

Yield: 4.6 g (13 mmol, 85%) of di(1-adamantyl)-n-butylphosphine. The product can be recrystallized from di-n-butyl ether (m.p.: 102° C.).

$^{31}$P{$^1$H} NMR (162.0 MHz, C$_6$D$_6$, 297 K): δ=24.6
MS (E.I., 70 eV):. m/z: 358 (M$^+$, 12%); 135 (Ad$^+$, 100%)
MS (C.I., isobutene): m/z: 359 (M$^+$+H, 100%)

Di(1-adamantyl)-n-butylphosphine (n-BuP(1-Ad)$_2$)
(Variant 3)

1.5 g (4.5 mmol) of di(1-adamantyl)chlorophosphine were placed in 40 ml of absolute THF, and 5 ml of a 1.6 M solution of n-BuLi in hexane (8 mmol) were added using a syringe, with stirring. The mixture was refluxed for 2 h, the solvent was distilled off under reduced pressure and the residue was distilled in a bulb tube. Yield: 0.77 g (2.1 mmol, 48%) of di(1-adamantyl)-n-butylphosphine.

Di(1-adamantyl)-n-butylphosphine (n-BuP(1-Ad)$_2$)
(Variant 4)

4.6 g (15 mmol) of di(1-adamantyl)phosphine were placed in 50 ml of di-n-butyl ether, and 20 ml of a 2.5 M solution of n-BuLi in toluene (50 mmol) were added. The mixture was refluxed for 1 h and cooled and 2.8 g (30 mmol) of 1-butyl chloride were added dropwise. The mixture was refluxed for 30 min, cooled and washed with saturated ammonium chloride solution (3×), the organic phase was separated off and dried over sodium sulfate and the solvent was distilled off under reduced pressure. The product was purified by bulb tube distillation under fine vacuum. Yield: 4.6 g (13 mmol, 85%) of di(1-adamantyl)-n-butylphosphine.

Example 2

Di(1-adamantyl)methylphosphine (MeP(1-Ad)$_2$)
(Variant 1)

11 ml of a 1.6 M solution of methyllithium in hexane (18 mmol) were added dropwise to 5.0 g (15 mmol) of diadamantylchlorophosphine in 250 ml of absolute tetrahydrofuran. The solution was refluxed for 1 h. After distillation of the solvent under vacuum, the residue was distilled under vacuum.

2.3 g (7.3 mmol, 49%) of diadamantylmethylphosphine were obtained.

Di(1-adamantyl)methylphosphine (MeP(1-Ad)2)
(Variant 2)

2.0 g (6.0 mmol) of di(1-adamantyl)chlorophosphine were placed in 50 ml of absolute THF, and 5 ml of a 1.6 M solution of MeLi in diethyl ether (8 mmol) were added using a syringe, with stirring. The mixture was refluxed for 2 h, the solvent was distilled off under reduced pressure and the residue was distilled in a bulb tube. Yield: 0.85 g (2.7 mmol, 45%) of di(1-adamantyl)methylphosphine (m.p.: 143° C.).

Elemental analysis: found (calc.): C: 79.52% (79.70%); H: 10.60% (10.51%); P: 9.78% (9.79%)

$^{31}$P{$^1$H} NMR (162.0 MHz, C$_6$D$_6$, 297 K): δ=7.8
MS (E.I., 70 eV): m/z: 316 (M$^+$, 36%); 135 (Ad$^+$, 100%)

Example 3

Di(1-adamantyl)-n-hexylphosphine (HexP(1-Ad)$_2$)
(Variant 1)

0.45 g of magnesium turnings (18 mmol) was placed in 150 ml of absolute tetrahydrofuran, and 3.0 g of 1-bromohexane (18 mmol) were added, with stirring, causing the ether to warm up. After the mixture had cooled to room temperature, a solution of 5.0 g of diadamantylchlorophosphine (15 mmol) in 100 ml of absolute tetrahydrofuran was added dropwise and the mixture was refluxed for 1 h. After distillation of the solvent under vacuum, the residue was distilled under high vacuum (0.01 mbar). Yield: 2.0 g (5.2 mmol, 35%) of diadamantyl-n-hexylphosphine.

Di(1-adamantyl)-n-hexylphosphine (HexP(1-Ad)2) (Variant 2)

5.5 g (18 mmol) of di(1-adamantyl)phosphine were placed in 60 ml of di-n-butyl ether, and 20 ml of a 2.5 M solution of n-BuLi (50 mmol) in toluene were added. The mixture was refluxed for 45 min and cooled and 3.0 g (18 mmol) of 1-bromohexane were added dropwise. The mixture was refluxed for 30 min, cooled and washed with saturated ammonium chloride solution (3×), the organic phase was separated off and dried over sodium sulfate and the solvent was distilled off under reduced pressure.

Yield: 4.9 g (13 mmol, 70%) of di(1-adamantyl)-n-hexylphosphine. The product can-be recrystallized from di-n-butyl ether.

$^{31}P\{^1H\}$ NMR (162.0 MHz, $C_6D_6$, 297 K): δ=24.6

MS: 386.31062 (calc. for $C_{26}H_{43}P$: 386.31024)

Example 4

Bis(diadamantylphosphino)butane (butylene(PAd$_2$)2)

0.45 g of magnesium turnings (18 mmol) was placed in 150 ml of absolute tetrahydrofuran, and 2.0 g of 1,4-dibromobutane (9.3 mmol) were added, with stirring, causing the ether to warm up. After the mixture had cooled to room temperature, a solution of 5.0 g of diadamantylchlorophosphine (15 mmol) in 100 ml of absolute tetrahydrofuran was added dropwise and the mixture was refluxed for 1 h. After distillation of the solvent under vacuum, the residue was distilled under high.vacuum (0.01 mbar). Yield: 1.0 g (1.5 mmol, 10%) of bis(diadamantylphosphino)butane.

Example 5

Di(1-adamantyl)-3-dimethylaminopropylphosphine 5.1 g (17 mmol) of di(1-adamantyl)phosphine were placed in 50 ml of di-n-butyl ether, and 20 ml of a 2.5 M solution of n-BuLi (50 mmol) in toluene were added. The mixture was refluxed for 1 h and cooled and 5.0 g (31 mmol) of 3-dimethylaminopropyl chloride hydrochloride were added, with cooling in an ice bath. The mixture was refluxed for 30 min, cooled and washed with saturated ammonium chloride solution (3×), the organic phase was separated off and dried over sodium sulfate and the solvent was distilled off. under reduced pressure. Yield: 4.6 g (12 mmol, 70%) of di(1-adamantyl)-3-dimethylaminopropylphosphine. The product can be recrystallized from di-n-butyl ether (m.p.: 138° C.).

Elemental analysis: found (calc.): C: 77.46% (77.47%); H: 11.09% (10.92%); N: 3.47% (3.61%); P: 7.78% (7.99%)

$^{31}P\{^1H\}$ NMR (162.0 MHz, $C_6D_6$, 297 K): δ=24.5

MS: 387.30528 (calc. for $C_{25}H_{42}NP$: 387.30548)

Example 6

Di(1-adamantyl)benzylphosphine 4.0 g (13 mmol) of di(1-adamantyl)phosphine were placed in 50 ml of di-n-butyl ether, and 18 ml of a 2.5 M solution of n-BuLi (45 mmol) in toluene were added. The mixture was refluxed for 30 min and cooled and 3.2 g (19 mmol) of benzyl bromide were added dropwise. The mixture was refluxed for 30 min, cooled and washed with saturated ammonium chloride solution (3×), the organic phase was separated off and dried over sodium sulfate and the solvent was distilled off under reduced pressure. Yield: 4.6 g (12 mmol, 90%) of di(1-adamantyl)benzylphosphine. The product is recrystallized from di-n-butyl ether (m.p.: 182° C.)

$^{31}P\{^1H\}$ NMR(162.0 MHz, $C_6D_6$, 297 K): δ=29.8

MS: 392.26420 (calc. for $C_{27}H_{37}P$: 392.26328)

Examples 7 to 20

General Operating Instructions for the Heck Reaction

In a pressure tube (obtainable e.g. from Aldrich), 5 mmol of aryl halide, 6 mmol of olefin, 6 mmol of base, a suitable amount of ligand and palladium(0)-dba complex and 500 mg of diethylene glycol di-n-butyl ether (as internal standard for GC analysis) were added to 5 ml of absolute dioxane under an argon atmosphere. The tube was sealed and suspended in a silicone oil bath at 120° C. After 24 h it was left to cool to room temperature. The solids were dissolved in 5 ml of methylene chloride and 5 ml of 2 N hydrochloric acid. The organic phase was analyzed by gas chromatography. The products were isolated by distillation, crystallization from methanol/acetone mixtures or column chromatography (silica gel, hexane/ethyl acetate mixtures).

TABLE 1

Heck reaction of p-chlorotoluene and styrene; n-BuPAd$_2$ as ligand

| No. | Base | Temp. (° C.) | Cat. conc. (mol %) | L:Pd | Conversion (%) | Yield (%) | TON |
|---|---|---|---|---|---|---|---|
| 7 | K$_3$PO$_4$ | 100 | 1.0 | 1:1 | 42 | 38 | 38 |
| 8 | K$_3$PO$_4$ | 100 | 1.0 | 2:1 | 39 | 25 | 25 |
| 9 | K$_3$PO$_4$ | 120 | 0.1 | 2:1 | 27 | 20 | 200 |
| 10 | K$_3$PO$_4$ | 120 | 1.0 | 2:1 | 98 | 98 | 98 |
| 11 | K$_3$PO$_4$ | 120 | 0.1 | 4:1 | 25 | 11 | 110 |
| 12 | K$_2$CO$_3$ | 120 | 1.0 | 2:1 | 78 | 68 | 68 |
| 13 | K$_3$PO$_4$ | 140 | 0.1 | 4:1 | 88 | 81 | 810 |

TABLE 2

Heck reaction of chlorobenzene and styrene at 120° C.; L:Pd = 2:1

| No. | Base | Cat. conc. (mol %) | Conversion (%) | Yield (%) | TON |
|---|---|---|---|---|---|
| 14 | K$_2$CO$_3$ | 1.0 | 71 | 63 | 63 |
| 15 | K$_3$PO$_4$ | 2.0 | 46 | 33 | 17 |

TABLE 3

Heck reaction with 2-ethylhexyl acrylate at 120° C.; base: K₃PO₄; 2.0 mol% of Pd (dba)₂; L:Pd = 2:1

| No. | Aryl chloride | Ligand | Conversion (%) | Yield (%) | TON |
|---|---|---|---|---|---|
| 16 | 4-Me-C₆H₄-Cl | n-BuPAd₂ | 66 | 63 | 32 |
| 17 | 4-MeO-C₆H₄-Cl | n-BuPAd₂ | 94 | 82 | 41 |
| 18 | 3-MeO-C₆H₄-Cl | n-BuPAd₂ | 51 | 34 | 17 |
| 19 | 3-F₃C-C₆H₄-Cl | n-BuPAd₂ | 38 | 12 | 6 |
| 20 | 2-Me-C₆H₄-Cl | n-BuPAd₂ | 48 | 44 | 22 |

Examples 21 to 40

General Operating Instructions for the Suzuki Reaction

In a pressure tube (obtainable e.g. from Aldrich), 3 mmol of aryl halide, 4.5 mmol of phenylboronic acid, 6 mmol of base, a suitable amount of ligand and palladium(II) acetate (P:Pd=2:1) and 100 mg of hexadecane (as internal standard for GC analysis) were dissolved in 6 ml of absolute toluene under an argon atmosphere. The tube was sealed and suspended in a-silicone oil bath at 100° C. After 20 h it was left to cool to room temperature. The solids were dissolved in 10 ml of methylene chloride and 10 ml of dilute sodium hydroxide solution. The organic phase was analyzed by gas chromatography. The products were isolated by crystallization from methanol/acetone mixtures or column chromatography (silica gel, hexane/ethyl acetate mixtures).

TABLE 4

Influence of the ligand on the coupling of 4-chlorotoluene and phenylboronic acid

| No. | PR₃ | Pd(OAc)₂ (mol %) | Yield (%) | TON |
|---|---|---|---|---|
| 21 | PPh₃ | 0.1 | 5 | 50 |
| 22 | PhPCy₂ | 0.1 | 23 | 230 |
| 23[a] | (o-tol) PCy₂ | 0.1 | 49 | 490 |
| 24[a] | (o-anisyl) PCy₂ | 0.1 | 42 | 420 |
| 25 | (o-biph) PCy₂ | 0.01 | 47 | 4700 |
| 26 | PCy₃ | 0.1 | 23 | 230 |
| 27 | PtBu₃ | 0.01 | 92 | 9200 |
| 28 | PtBu₃ | 0.005 | 41 | 8200 |
| 29 | BuPAd₂ | 0.01 | 94 | 9400 |
| 30 | BuPAd₂ | 0.005 | 87 | 17,400 |

[a]P:Pd = 4:1

TABLE 5

Suzuki coupling of various aryl chlorides (R-C₆H₄—Cl) with phenylboronic acid in the presence of 0.005 mol % of Pd(OAc)₂/2 BuPAd₂

| No. | R | Yield (%) | TON |
|---|---|---|---|
| 31 | 4-Me | 87 | 17,400 |
| 32[a] | 4-Me | 74 | 14,800 |
| 33 | 2-Me | 85 | 17,000 |
| 34 | 2,6-Me2 | 68 | 13,600 |
| 35 | H | 80 | 16,000 |
| 36 | 2-F | 96 | 19,200 |
| 37 | 4-MeO | 64 | 12,800 |
| 38 | 3-MeO | 58 | 11,600 |
| 39 | 2-CN | 100 | 20,000 |
| 40 | "3-N,"[b] | 99 | 19,800 |

[a]4 instead of 20 h;
[b]3-chloropyridine

Examples 41 to 54

General Operating Instructions for Catalytic Amination

In a pressure tube (obtainable e.g. from Aldrich), 5 mmol of aryl halide, 6 mmol of amine, 6 mmol of sodium tert-butylate and a suitable amount of ligand and palladium (0)-dibenzylidenacetone complex were added to 5 ml of absolute toluene under an argon atmosphere. The tube was sealed and suspended in a silicone oil bath at 120° C. After 20 h it was left to cool to room temperature. The solids were dissolved in 5 ml of CH₂Cl₂ and 5 ml of 2 N hydrochloric acid, and 500 mg of diethylene glycol di-n-butyl ether were added as internal GC standard. The organic phase was analyzed by gas chromatography. The products were isolated by distillation, crystallization from methanol/acetone mixtures or column chromatography (silica gel, hexane/ethyl acetate mixtures).

TABLE 6

Catalytic amination of aryl halides;
0.5 mol % of Pd(dba)$_2$, n-BuPAd$_2$

| No. | Aryl chloride | Amine | Product | Yield [%] |
|---|---|---|---|---|
| 41 | 2-chloro-m-xylene | 2,6-dimethylaniline | bis(2,6-dimethylphenyl) amine | 84 |
| 42 | 2-chloro-m-xylene | 2,6-diisopropylaniline | 2,6-dimethylphenyl-2',6'-diisopropylaniline | 70 |
| 43 | 2-chlorofluorobenzene | 2,6-diisopropylaniline | 2-fluorophenyl-2',6'-diisopropylaniline | 70 |
| 44 | 2-chloro-m-xylene | 1-adamantylamine | N-(1-adamantyl)-2,6-dimethylaniline | 84 |
| 45 | 2-chloro-m-xylene | tert-butylamine | N-(tert-butyl)-2,6-dimethylamine | 93 |
| 46 | chlorobenzene | diethylamine | N,N-diethylaniline | 44 |
| 47 | chlorobenzene | di-n-butylamine | N,N-di-n-butylaniline | 72 |
| 48 | 3-chlorotoluene | diethylamine | N,N-diethyl-m-toluidine | 49 |
| 49 | 3-chloroanisole | diethylamine | N,N-diethyl-m-methoxyaniline | 58 |
| 50 | 4-chlorotoluene | diethylamine | N,N-diethyl-p-toluidine | 40 |
| 51 | chlorobenzene | piperidine | N-phenylpiperidine | 76 |
| 52 | chlorobenzene | morpholine | N-phenylmorpholine | 87 |
| 53 | o-chloroanisole | 2,6-dimethylaniline | 2-methoxyphenyl-2,6-dimethylaniline | 100 |
| 54 | o-chloroanisole | 2,6-diisopropylaniline | 2-methoxyphenyl-2,6-diisopropylaniline | 88 |

Examples 55 to 59

Catalytic α-arylation of Ketones:

In a pressure tube (obtainable e.g. from Aldrich), 5 mmol of aryl halide, 6 mmol of ketone, 6 mmol of sodium tert-butylate and a suitable amount of ligand and palladium (II) acetate were added to 5 ml of absolute toluene under an argon atmosphere. The tube was sealed and suspended in a silicone oil bath at 80° C. After 20 h it was left to cool to room temperature. The solids were dissolved in 5 ml of CH$_2$Cl$_2$ and 5 ml of 2 N hydrochloric acid, and 500 mg of diethylene glycol di-n-butyl ether were added as internal GC standard. The organic phase was analyzed by gas chromatography. The products were isolated by distillation, crystallization from methanol/acetone mixtures or column chromatography (silica gel, hexane/ethyl acetate mixtures).

TABLE 7

Catalytic α-arylation of ketones; 1 mol % of PdOAc$_2$; 2 mol % of n-BuPAd$_2$

| No. | Aryl-X | T (20 C.) | Ketone | Conversion (%) |
|---|---|---|---|---|
| 55 | chlorobenzene | 120 | acetophenone | 100 |
| 56 | p-chlorotoluene | 80 | deoxybenzoin | 66 |
| 57 | p-chloro- | 80 | propiophenone | 99 |

TABLE 7-continued

Catalytic α-arylation of ketones; 1 mol % of PdOAc$_2$; 2 mol % of n-BuPAd$_2$ toluene

| # | Aryl halide | Yield (%) | Ketone | Conv. (%) |
|---|---|---|---|---|
| 58 | H$_3$C—⟨=⟩—Cl<br>p-chloro-toluene | 80 | (3-pentanone) | 100 |
| 59 | ⟨=⟩(Cl)(Cl)<br>1,2-dichlorobenzene | 80 | (3-pentanone) | 100 |

| Product 1 (mono-arylated) | Yield$^a$ (%) | Product 2 (bis-arylated) | Yield$^a$ (%) |
|---|---|---|---|
| deoxybenzoin | 70 | diphenylmethane | 28 |
| ./. |  | 1,2-diphenyl-2-p-tolyl-ethanones | 65 |
| 1-phenyl-2-p-tolyl-propan-1-ones | 97 | ./. |  |
| 2-p-tolyl- | 54 | not isolated | no data |

TABLE 7-continued

Catalytic α-arylation of ketones; 1 mol % of PdOAc₂; 2 mol % of n-BuPAd₂

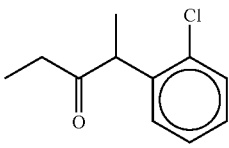

pentan-3-ones 58    not isolated    no data 2-(2'-chloro-phenyl)-pentan-3-ones

Examples 60 to 79

Further Catalysis Examples of the α-arylation of Ketones

In a pressure tube (obtainable e.g. from Aldrich), 5 mmol of aryl halide, 6 mmol of ketone, 6 mmol of tripotassium phosphate and a suitable amount of ligand and palladium(II) acetate were added to 5 ml of absolute dioxane under an argon atmosphere. The tube was sealed and suspended in a silicone oil bath at 100° C. After 20 h it was left to cool to room temperature. The solids were dissolved in 5 ml of $CH_2Cl_2$ and 5 ml of 2 N hydrochloric acid, and 500 mg of diethylene glycol di-n-butyl ether were added as internal GC standard. The organic phase was analyzed by gas chromatography. The products were isolated by distillation, crystallization from methanol/acetone mixtures or column chromatography (silica gel, hexane/ethyl acetate mixtures).

TABLE 8

Reaction of chlorobenzene with acetophenone; 1 mol% of PdOAc₂

| No. | Ligand | Temp. | Conversion (%) | Yield (%) of deoxybenzoin | Yield (%) of 1,2,2-triphenyl-ethanone |
|---|---|---|---|---|---|
| 60 | BuPAd₂ | 100 | 83 | 16 | 51 |
| 61 | N,N-dimethyl- | 100 | 68 | 6 | 44 |

TABLE 8-continued

Reaction of chlorobenzene with acetophenone; 1 mol% of PdOAc₂

| No. | Ligand | Temp. | Conversion (%) | Yield (%) of deoxybenzoin | Yield (%) of 1,2,2-triphenyl-ethanone |
|---|---|---|---|---|---|
| | aminopropyl-PAd₂ | | | | |
| 62 | phenyl-PCy₂ | 100 | 72 | 31 | 31 |
| 63 | PCy₃ | 100 | 74 | 33 | 32 |
| 64 | o-biphenyl-PCy₂ | 100 | 50 | 17 | 19 |
| 65 | BuPCy₂ | 100 | 31 | 17 | 3 |
| 66 | P(t-Bu)₃ | 100 | 37 | 0 | 19 |

TABLE 8-continued
Reaction of chlorobenzene with acetophenone; 1 mol% of PdOAc$_2$
| No. | Ligand | Temp. | Conversion (%) | Yield (%) of deoxybenzoin | Yield (%) of 1,2,2-triphenyl-ethanone |
|---|---|---|---|---|---|
| 67 | 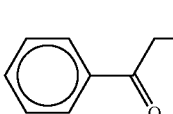 Bup(t-Bu)$_2$ | 100 | 44 | 9 | 20 |
| 68 | 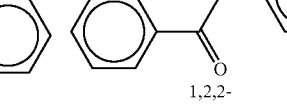 PPh$_3$ | 100 | 17 | 2 | 0 |
TABLE 9
α-Arylation of ketones; 1 mol % of PdOAc$_2$; 2 mol % of n-BuPAd$_2$
| No. | Aryl-X | T (° C.) | Ketone | Conversion (%) |
|---|---|---|---|---|
| 69 | 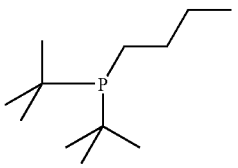 chlororbenzene | 100 | 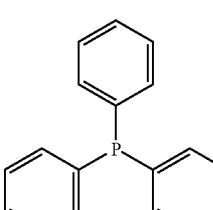 acetophenone | 83 |
| 70 | 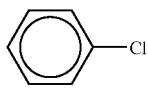 p-chlorotoluene | 100 | 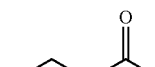 deoxybenzoin | 100 |

TABLE 9-continued

α-Arylation of ketones; 1 mol % of PdOAc$_2$; 2 mol % of n-BuPAd$_2$

| # | Aryl chloride | T/conv | Ketone | Yield |
|---|---|---|---|---|
| 71 | p-chlorotoluene (H$_3$C–C$_6$H$_4$–Cl) | 120 / 100 | propiophenone | 100 / 48 |
| 72 | p-chlorotoluene (H$_3$C–C$_6$H$_4$–Cl) | 100 | 1-indanone | 100 |
| 73 | p-chlorotoluene (H$_3$C–C$_6$H$_4$–Cl) | 100 | 3-pentanone | 42 |
| 74 | p-chlorotoluene (H$_3$C–C$_6$H$_4$–Cl) | 100 | cyclohexanone | 100 |
| 75 | p-chloroanisole (H$_3$CO–C$_6$H$_4$–Cl) | 100 | acetophenone | 100 |

| Product 1 (monoarylated) | Yield[a] (%) | Product 2 (bis-arylated) | Yield[a] (%) |
|---|---|---|---|
| deoxybenzoin | 16 | 1,2,2-triphenylethanone | 51 |

TABLE 9-continued
α-Arylation of ketones; 1 mol % of PdOAc$_2$; 2 mol % of n-BuPAd$_2$
| | | | |
|---|---|---|---|
| ./. | 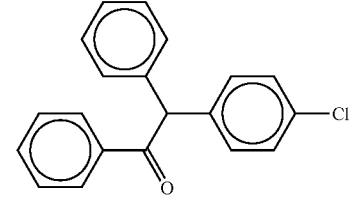<br>1,2-diphenyl-2-p-tolyl-ethanones | 100 | |
| 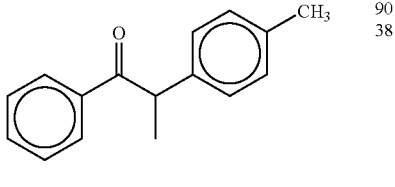<br>1-phenyl-2-p-tolyl-propan-1-ones | 90<br>38 | ./. | |
| 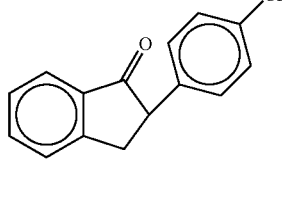<br>2-p-tolyl-1-indanone | 42 | 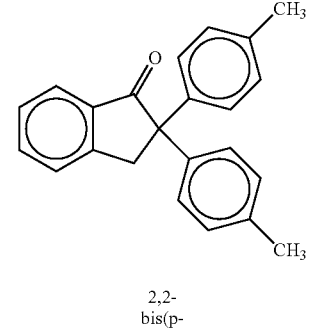<br>2,2-bis(p-tolyl)-1-indanone | 32 |
| 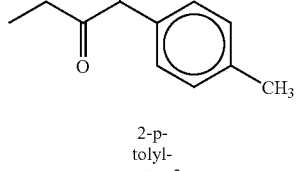<br>2-p-tolyl-pentan-3-ones | 27 | not<br>isolated | no data |
| 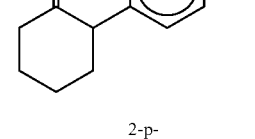<br>2-p-tolyl-cyclohexanones | 38 | ./. | |

TABLE 9-continued

α-Arylation of ketones; 1 mol % of PdOAc$_2$; 2 mol % of n-BuPAd$_2$

| 25 | 57 |
|---|---|
| 2-p-anisyl-1-phenyl-ethanones | 2,2-bis-p-anisyl-1-phenyl-ethanone |

Example 80

Coupling of Aryl Chlorides with Organozinc Compounds 50 mmol of anhydrous zinc chloride (dissolved in 40 ml of THF) were added at 0° C to a suspension of 50 mmol of ethynyllithium-ethylenediamine complex in 40 ml of THF. After heating to RT for half an hour, the solution was again cooled to 0° C. and 40 mmol of 4-chloroanisole, 0.05 mol % of Pd(OAc)$_2$ and 0.1 mol % of butyldiadamantylphosphine were added. The reaction mixture was stirred at 25 to 50° C. until conversion was complete. 2 M HCl solution was then added to the reaction solution. After extraction with ether, washing of the ether phase and distillation, 76% of p-methoxyphenylacetylene is obtained.

Example 81

Coupling with Alkynes 0.005 mol % of Pd(OAc)$_2$, 0.01 mol % of hexyldiadamantyl-phosphine and 1 mol % of Cu(I)I are added to a mixture of 12 mmol of trimethylsilylacetylene and 10 mmol of 4-chloronitrobenzene in 40 ml of diethylamine. The mixture is stirred under reflux until conversion is complete. The readily volatile constituents are then removed under vacuum. The residue is dissolved in toluene and washed with water. After chromatography on silica gel, 89% of 1-(4-nitrophenyl)-2-trimethylsilylacetylene is obtained.

Example 82

Heck Coupling with Ethylene 50 mmol of 6-methoxy-2-bromonaphthalene and 60 mmol of potassium carbonate are dissolved in 40 ml of NMP, and 0.001 mol % of Pd(OAc)$_2$ and 0.004 mol % of butyldiadamantyl-phosphine are added. The mixture is placed under an ethylene pressure of 20 bar and stirred at 130° C. until conversion is complete. After filtration of the insoluble constituents, washing with alkaline solution and distillation, 92% of 6-methoxy-2-vinylnaphthalene is obtained.

Example 83

Carbonylation Reaction 20 mmol of 6-methoxy-2-bromonaphthalene and 30 mmol of triethylamine are dissolved in 30 ml of 1-butanol, and 0.05 mol % of Pd(OAc)$_2$ and 0.1 mol % of butyldiadamantylphosphine are added. The mixture is placed under a CO pressure of 3 bar and stirred at 130° C. until conversion is complete.

After filtration of the insoluble constituents, washing with alkaline solution and distillation, 94% of butyl 6-methoxy-2-naphthalenecarboxylate is obtained.

The invention claimed is:

1. A catalyst comprising:
(a) a phosphine ligand of formula Ia:

(adamantyl)$_n$P(alkyl)$_m$    Ia in which adamantyl is an adamantyl radical (IIa or IIb) bonded to the phosphorus atom in the 1- or 2-position:

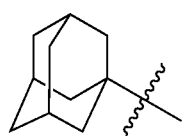

IIa

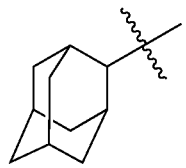

IIb alkyl is a C$_3$ to C$_{18}$ alkyl group, and
wherein said alkyl group, and said adaxnantyl radical independently of one another can have, in addition to hydrogen atoms, up to 10 substituents which, independently of one another, are selected from the group consisting of: C$_1$ to C$_8$ alkyl, O-alkyl(C$_1$–C$_8$), OH, OCO-alkyl(C$_1$–C$_8$), O-phenyl, phenyl, alyl, fluorine, NO$_2$, Si-(alkyl(C$_1$–C$_8$))$_3$, CN, COOH, CHO, SO$_3$H, NH$_2$, NH-alkyl (C$_1$–C$_8$), (alkyl(C$_1$–C$_8$)$_2$, P(alkyl (C$_1$–C$_8$))$_2$, P(aryl)$_2$, SO$_2$alkyl(C$_1$–C$_6$), SO-alkyl (C$_1$–C$_6$), CF$_3$, NHCO-alkyl(C$_1$–C$_4$), COO-alkyl (C$_1$–C$_8$), CONH$_2$, CO-alkyl(C$_1$–C$_8$), NHCHO, NHCOO-alkyl(C$_1$–C$_4$), CO-phenyl, COO-phenyl, CH=CH—CO$_2$-alkyl(C$_1$–C$_8$), CH=CHCOOH, PO(phenyl)$_2$, PO(alkyl(C$_1$–C$_4$))$_2$, PO$_3$H$_2$, PO(O-alkyl(C$_1$–C$_6$))$_2$ or SO$_3$(alkyl(C$_1$–C$_4$)), wherein said aryl is an aromatic with 5 to 14 ring carbon atoms, and wherein one or more of said ring carbon atoms may be replaced by nitrogen, oxygen and/or sulfur atoms to give a heteroaromatic with 1 to 13 ring carbon atoms, where n is a number between 1 and 3; m is a number between 0 and 2; and wherein n+m=3; and (b) a transition metal of subgroup VIII of the Periodic Table of the Elements, wherein said metal may optionally be in the form of a salt or in a complex with said phosphine ligand.

2. The catalyst of claim 1, wherein said alkyl is an C$_3$ to C$_6$ alkyl group.

3. The catalyst of claim 2, wherein said alkyl is unbranched and wherein n=2 and m=1.

4. The catalyst of claim 3, wherein said transition metal is selected from the group consisting of; palladium; nickel; platinum; rhodium; iridium; ruthenium; and cobalt.

5. The catalyst of claim 4, wherein said transition metal is nickel.

6. The catalyst of claim 4, wherein said transition metal is palladium.

7. The catalyst of claim 3, wherein said catalyst is in the form of a complex comprising a mono-, di-, tri-, or tetra-phosphine and said transition metal.

8. The catalyst of claim 3, wherein the ratio of transition metal to ligand is in the range of 1:1 to 1:100.

9. The catalyst of claim 3, wherein, each adamantyl group is independently either unsubstituted or substituted with up to three substituents selected from the group consisting of: C$_1$–C$_8$ alkyl; O-alkyl (C$_1$–C$_8$); OH; OCO-alkyl (C$_1$–C$_8$); phenyl; O-phenyl; COOH; SO$_3$H; NH$_2$; P(alkyl(C$_1$–C$_8$))$_2$; P(phenyl)$_2$; COO-alkyl(C$_1$–C$_8$); CONH$_2$; and PO(phenyl)$_2$.

10. The catalyst of claim 9, wherein, each adamantyl group is unsubstituted and said alkyl is a C$_4$–C$_6$ alkyl group.

11. A catalyst comprising:
(a) a phosphine ligand of formula Ib:

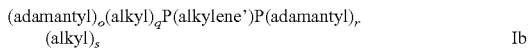

in which adamantyl is an adamantyl radical (IIa or IIb) bonded to the phosphorus atom in the 1- or 2-position:

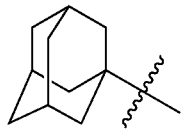

IIa

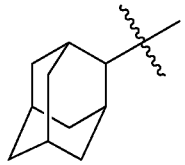

IIb alkyl is a C$_3$ to C$_{18}$ alkyl group, and alkylene'is a bridging methylene, 1,2-ethylene, 1,3-propylene, 1,4-butylene, 1,5-pentylene or 1,6-hexylene bridge, 1,2-diphenylene, 2,2'-substituted 1,1'-binaphthyl or ferrocenyl bridge, where said alkyl group, said alkylene'group and said adamantyl radical independently of one another can have, in addition to hydrogen atoms, up to 10 substituents which, independently of one another, are selected from the group consisting of: C$_1$ to C$_8$ alkyl, O-alkyl(C$_1$–C$_8$), OH, OCO-alkyl(C$_1$–C$_8$), O-phenyl, phenyl, aryl, fluorine, NO$_2$, Si-(alkyl(C$_1$–C$_8$))$_3$, CN, COOH, CHO, SO$_3$H, NH$_2$, NH-alkyl(C$_1$–C$_8$), (alkyl (C$_1$–C$_8$)$_2$, P(alkyl(C$_1$–C$_8$))$_2$, P(aryl)$_2$, SO$_2$-alkyl (C$_1$–C$_6$), SO-alkyl(C$_1$–C$_6$), CF$_3$, NHCO-alkyl (C$_1$–C$_4$), COO-alkyl(C$_1$–C$_8$), CONH$_2$, CO-alkyl (C$_1$–C$_8$), NHCHO, NHCOO-alkyl(C$_1$–C$_8$), CO-phenyl, COO-phenyl, CH=CH—CO$_2$-alkyl (C$_1$–C$_8$), CH=CHCOOH, PO(phenyl)$_2$, PO(alkyl(C$_1$–C$_4$))$_2$, PO$_3$H$_2$, PO(O-alkyl(C$_1$–C$_6$))$_2$ or SO$_3$(alkyl(C$_1$–C$_4$)), wherein said aryl is an aromatic with 5 to 14 ring carbon atoms, and wherein one or more of said ring carbon atoms may be replaced by nitrogen, oxygen and/or sulfur atoms to give a heteroaromatic with 1 to 13 ring carbon atoms, where o and r are the number either 1 or 2; q and s are the number 0 or 1; and wherein o+q =2, and r+s=2; and (b) a transition metal of subgroup VIII of the Periodic Table of the Elements, wherein said metal may optionally be in the form of a salt or in a complex with said phosphine ligand.

12. The catalyst of claim 11, wherein said alkyl is a C$_3$ to C$_6$ alkyl group.

13. The catalyst of claim 12, wherein said alkyl is unbranched and wherein o=2 and r=2.

14. The catalyst of claim 13, wherein said transition metal is selected from the group consisting of: palladium; nickel; platinum; rhodium; iridium; ruthenium; and cobalt.

15. The catalyst of claim 14, wherein said transition metal is nickel.

16. The catalyst of claim 14, wherein said transition metal is palladium.

17. The catalyst of claim 13, wherein said catalyst is in the form of a complex comprising a mono-, di-, tri-, or tetra-phosphine and said transition metal.

18. The catalyst of claim 13, wherein the ratio of transition metal to ligand is in the range of 1:1 to 1:100.

19. The catalyst of claim 13, wherein, each adamantyl group is independently either unsubstituted or substituted with up to three substituents selected from the group consisting of: C$_1$–C$_8$ alkyl; O-alkyl(C$_1$–C$_8$); OH; OCO-alkyl (C$_1$–C$_8$); phenyl; O-phenyl; COOH; SO$_3$H; NH$_2$; P(alkyl (C$_1$–C$_8$))$_2$; P(phenyl)$_2$; COO-alkyl(C$_1$–C$_8$); CONH$_2$; and PO(phenyl)$_2$substituted with one or two C$_1$–C$_8$ alkyls.

20. The catalyst of claim 19, wherein, each adamantyl group is unsubstituted and said alkyl is a C$_4$–C$_6$ alkyl group.

* * * * *